United States Patent
Tu et al.

(10) Patent No.: US 6,346,647 B2
(45) Date of Patent: Feb. 12, 2002

(54) CATALYST FOR THE PRODUCTION OF ACRYLIC ACID

(75) Inventors: Xinlin Tu; Mamoru Takahashi; Madoka Furuta; Hiroshi Niizuma, all of Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 09/828,235

(22) Filed: Apr. 9, 2001

Related U.S. Application Data

(62) Division of application No. 09/521,853, filed on Mar. 9, 2000.

(30) Foreign Application Priority Data

Mar. 10, 1999 (JP) .............................................. 11-62488

(51) Int. Cl.$^7$ ........................................... C07C 51/215
(52) U.S. Cl. ..................................................... 562/549
(58) Field of Search ......................................... 562/549

(56) References Cited

U.S. PATENT DOCUMENTS

| | | | |
|---|---|---|---|
| 4,250,346 A | 2/1981 | Young et al. ................. | 585/658 |
| 4,257,921 A | 3/1981 | Slinkard et al. ............. | 502/302 |
| 4,311,611 A | 1/1982 | Sasaki et al. ................ | 252/412 |
| 4,524,236 A | 6/1985 | McCain ....................... | 585/658 |
| 4,677,225 A | 6/1987 | Niizuma et al. ............. | 562/599 |
| 5,432,141 A | 7/1995 | Brazdil, Jr. et al. ......... | 502/311 |
| 5,750,777 A | 5/1998 | Aubry et al. ................ | 562/549 |
| 5,959,143 A | 9/1999 | Sugi et al. ................... | 562/534 |
| 5,994,580 A * | 11/1999 | Takahashi et al. | |
| 6,036,880 A | 3/2000 | Komada et al. ........ | 252/183.13 |
| 6,043,184 A | 3/2000 | Karmakar et al. .......... | 502/208 |
| 6,060,422 A | 5/2000 | Takahashi et al. .......... | 502/312 |
| 6,063,728 A | 5/2000 | Hinago et al. .............. | 502/300 |
| 6,143,690 A | 11/2000 | Komada et al. ............ | 502/211 |
| 6,291,393 B1 * | 9/2001 | Tu et al. | |

* cited by examiner

*Primary Examiner*—Gary Geist
*Assistant Examiner*—Robert W. Deemie
(74) *Attorney, Agent, or Firm*—Sughrue Mion, PLLC

(57) ABSTRACT

A metal oxide catalyst which can produce acrylic acid by a vapor phase catalytic oxidation of propane in high yield and has excellent abrasion resistance is disclosed. The metal oxide catalyst comprises Mo, V, Sb, A (A represents Nb or Ta) and optionally other metals, and is prepared through the following steps (1) and (2):

(1) Step of reacting $V^{+5}$ and $Sb^{+3}$ at a temperature of 70° C. or higher in the presence of $Mo^{+6}$ in an aqueous medium, and bubbling an oxygen-containing gas into the reaction solution during or after the reaction; and (2) Step of adding to the reaction product obtained in step (1) a solution containing a compound comprising A and an aqueous solution of nitric acid or ammonium nitrate, uniformly stirring these components, and then calcining the resulting mixture.

2 Claims, No Drawings

CATALYST FOR THE PRODUCTION OF ACRYLIC ACID

This is a divisional of application Ser. No. 09/521,853, filed Mar. 9, 2000, the disclose of which is incorporated herein by reference.

FIELD OF THE INVENTION

The present invention relates to a metal oxide catalyst for use in the production of acrylic acid by a vapor phase catalytic oxidation of a hydrocarbon having three carbon atoms such as propane and propylene.

BACKGROUND OF THE INVENTION

In general, acrylic acid is produced through a two-stage oxidation process comprising a step of catalytic reaction of propylene with oxygen to acrolein and a step of catalytic reaction of acrolein with oxygen to acrylic acid.

In recent years, on the other hand, for the reason that there is a difference in price between propane and propylene or the two-stage oxidation of propylene requires complicated steps, the production of acrylic acid using propane as a starting material through a one-stage process has been studied. Many proposals have been made on the catalyst for use in such a process. Representative examples of proposed catalysts include [V, P, Te]-based catalyst [as disclosed in "Catalysis Today", 13, 679 (1992)], AgBiVMoO (as disclosed in JP-A-2-83348 (The term "JP-A" as used herein means an "unexamined published Japanese patent application")), $BiMo_{12}V_5Nb_{0.5}SbKO_n$ (as disclosed in U.S. Pat. No. 5,198,580), [Mo, Te, V, Nb]-based catalyst (as disclosed in JP-A-6-279351), and [Mo, Sb, V, Nb]-based catalyst (as disclosed in JP-A-9-316023 and JP-A-10-137585).

Furthermore, JP-A-10-230164 discloses an improvement in the catalyst for the production of acrylic acid disclosed in the above cited JP-A-9-316023 and JP-A-10-137585, i.e., process for the production of [Mo, Sb, V, Nb]-based oxide catalyst involving a first step of reacting $V^{+5}$ and $Sb^{+3}$ at a temperature of 70° C. or higher in the presence of $Mo^{+6}$ in an aqueous medium and bubbling molecular oxygen or a gas containing molecular oxygen through the reaction solution during or after the reaction and a second step of mixing an Nb compound with the reaction mixture and then calcining the mixture.

However, the above proposed catalyst is disadvantageous in that the yield of acrylic acid as the desired product is insufficient or life of the catalyst itself is short. For example, the [Mo, Te, V, Nb]-based catalyst proposed in the above cited JP-A-6-279351 allows the production of acrylic acid in a high yield but is liable to evaporate Te, thereby causing deterioration of catalytic activity with the lapse of time. Further, the [Mo, Sb, V, Nb]-based catalyst disclosed in JP-A-9-316023 and JP-A-10-230164 still has further improvement in the yield of acrylic acid or the reproducibility of production of catalyst. Further, where those catalysts are used for fluidized bed reaction, it is required for the catalysts to exhibit excellent catalytic properties as well as excellent abrasion resistance. Those catalysts are still insufficient in this respect.

SUMMARY OF THE INVENTION

As a result of extensive studies to overcome the above-described problems, it has been found that a catalyst which exhibits an excellent abrasion resistance and gives a high yield of acrylic acid can be obtained by adding an aqueous solution of nitric acid or ammonium nitrate together with an Nb compound or a Ta compound at the second step in the process for the production of a metal oxide catalyst for the production of acrylic acid disclosed in the above cited JP-A-10-230164. The present invention has been completed based on this finding.

It is therefore an object of the present invention to provide a metal oxide catalyst which can give a high yield and exhibits an excellent abrasion resistance in the production of acrylic acid by a vapor phase catalytic oxidation of propane.

A first embodiment of the present invention is to provide a metal oxide catalyst comprising Mo, V, Sb, A (A represents Nb or Ta) and optionally other metals for the production of acrylic acid by a vapor phase catalytic reaction of propane, which is prepared through the following steps (1) and (2):

(1) Step of reacting $V^{+5}$ and $Sb^{+3}$ at a temperature of 70° C. or higher in the presence of $Mo^{+6}$ in an aqueous medium, and bubbling an oxygen-containing gas into the reaction mixture during or after the reaction; and (2) Step of adding to the reaction product obtained in step (1) a solution containing a compound comprising A and an aqueous solution of nitric acid or ammonium nitrate, uniformly stirring these components, and then calcining the resulting mixture.

A second embodiment of the present invention is to provide the above-described metal oxide catalyst wherein bubbling the oxygen-containing gas into the reaction solution obtained in step (1) is replaced by addition of hydrogen peroxide to the reaction solution obtained in step (1).

DETAILED DESCRIPTION OF THE INVENTION

The present invention will be described in more detail below.

In the step (1) of the present invention, the three reactants $Sb^{+3}$, $V^{+5}$ and $Mo^{+6}$ undergo oxidation-reduction reaction at a temperature of 70° C. or higher in an aqueous medium. This reaction does not proceed unless heated at a temperature of 70° C. or higher. The reaction temperature is preferably in the vicinity of the boiling point of the aqueous medium. The reaction time is preferably from about 5 to 15 hours.

The main elementary reaction in the above reaction is represented by the following formulae (a) and (b):

$$V^{+5}+Sb^{+3}\rightarrow V^{+3}+Sb^{+5} \qquad (a)$$

$$V^{+3}+Mo^{+6}\rightarrow V^{+4}+Mo^{+5} \qquad (b)$$

When the oxygen-containing gas is blown into the reaction solution or hydrogen peroxide is added to the reaction solution during or after the reaction, $Mo^{+5}$ produced by the reaction (b) is reconverted to $Mo^{+5}$, making it possible to appropriately control the concentration of $Mo^{+5}$. This makes it possible to produce a catalyst giving a high yield of acrylic acid.

The $V^{+5}$ compound comprising $V^{+5}$ used in the above reaction is preferably ammonium metavanadate or vanadium pentaoxide. The $Sb^{+3}$ compound comprising $Sb^{+3}$ is preferably antimony trioxide or antimony acetate. The $Mo^{+6}$ compound comprising $Mo^{+6}$ is ammonium molybdate, molybdenum oxide or molybdic acid, and ammonium molybdate is preferably from the standpoint that it is water-soluble.

The preferred proportion of $Mo^{+6}$ compound, $V^{+5}$ compound and $Sb^{+3}$ compound used in the oxidation-reduction reaction is such that the atomic ratio of Mo, V and Sb constituting the desired catalyst corresponds to the following empirical formula:

$$MoV_iSb_j$$

wherein i and j each represent a number of from 0.01 to 1.5.

The suffixes i and j each preferably represent a number of from 0.1 to 1. If i and j in the above compositional formula each are below 0.01 or exceed 1.5, the conversion of propane and the selectivity of acrylic acid in the reaction for the production of acrylic acid are decreased.

The preferred proportion of $V^{+5}$ compound and $Sb^{+3}$ compound used in the oxidation-reduction reaction is from 0.3 to 1:1 in terms of atomic ratio of $Sb^{+3}$ to $V^{+5}$. If the proportion of $Sb^{+3}$ is below 0.3, the selectivity of acrylic acid is lowered. On the other hand, if the proportion of $Sb^{+3}$ exceeds 1, the conversion of propane is lowered.

The preferred charged amount of the metal compound in the aqueous medium is from 3 to 30 parts by weight per 100 parts by weight of water as calculated in terms of total amount of three metal compounds. When the total amount of the three metal compounds exceeds 30 parts by weight, the V compound or Mo compound partly becomes insoluble, possibly making the oxidation-reduction reaction incomplete.

The progress of the reaction can be known by quantitatively analyzing pentavalent Sb in the reaction mixture, and then comparing the analysis with the initially charged amount of trivalent Sb. In some detail, a 1 N aqueous solution of oxalic acid in an amount of 10 times or more than that of the reaction solution was added to the reaction solution thus obtained to precipitate and separate only Sb. The resulting precipitate is titrated with hydroiodic acid, so that pentavalent Sb can be quantitatively analyzed.

The valency of Mo and V in the reaction solution can be determined by electron spin resonance spectrum or the like.

In the step (1) of the invention, the oxygen-containing gas is bubbled into the oxidation-reduction reaction solution as described above. Bubbling the oxygen-containing gas into the oxidation-reduction reaction solution may be conducted during or after the oxidation-reduction reaction. The reaction solution is preferably stirred during bubbling the oxygen-containing gas.

The term "oxygen-containing gas" used herein means pure oxygen gas, air or a gas containing oxygen gas.

The concentration of oxygen gas in the oxygen-containing gas is preferably 0.5 vol % or more, more preferably from 1 to 20 vol %, and most preferably from 2 to 15 vol % (hereinafter referred to as "%" for brevity). When the concentration of oxygen gas in the oxygen-containing gas is below 0.5%, the catalyst finally obtained may have a low activity.

The preferred bubbling rate (flow rate) of the oxygen-containing gas depends on the reacted amount of the oxidation-reduction reaction solution. When the reacted amount of the oxidation-reduction reaction solution is from 200 ml to 500 ml, the preferred bubbling rate is from 3 to 12 liter/hr.

The bubbling time of the oxygen-containing gas into the reaction solution is preferably 4 hours or more. The bubbling time is more preferably from 5 to 10 hours. If the bubbling time is shorter than 4 hours, the resulting catalyst may have a low activity.

Where bubbling the oxygen-containing gas is replaced by the addition of hydrogen peroxide to the oxidation-reduction reaction solution as in step (3) of the second embodiment of the present invention, any compound containing hydrogen peroxide may be used. For example, pure hydrogen peroxide or aqueous hydrogen peroxide may be used. Preferably, aqueous hydrogen peroxide is used. More preferably, aqueous hydrogen peroxide having a hydrogen peroxide concentration of from 0.01 to 35% by weight is used.

The optimum amount of hydrogen peroxide added depends on the amount of Sb compound in the raw material. When the amount of Sb is 1 as calculated in terms of molar ratio, the amount of hydrogen peroxide is preferably from 0.2 to 1.2.

The addition of hydrogen peroxide to the oxidation-reduction reaction solution may be conducted during or after the oxidation-reduction reaction, but the addition after the oxidation-reduction reaction is particularly preferable.

The step (2) in the first embodiment of the present invention or the step (4) in the second embodiment of the present invention comprises adding an Nb compound or Ta compound to the dispersion of Mo, V and Sb which is a reaction product of the above reaction or a residue of evaporation thereof to dryness, and uniformly mixing the resulting mixture. Examples of such an Nb compound or Ta compound used include niobium oxide, niobic acid, tantalum oxide and tantalic acid. The Nb compound or Ta compound may be used in the form of dispersion in water. Preferably, the Nb compound or Ta compound is used in the form of aqueous solution of oxalate containing oxalic acid as well. Where the Nb compound or Ta compound is added in the form of aqueous solution of oxalate, the amount of oxalic acid used is preferably from 4 to 12 to metallic Nb or Ta as calculated in terms of molar ratio.

In the present invention, an aqueous solution of nitric acid or ammonium nitrate besides the Nb compound or Ta compound is added to the reaction product obtained in the step (1). The order of addition of these components is that the Nb compound or Ta compound may be added together with the aqueous solution of nitric acid or ammonium nitrate or before addition of the aqueous solution of nitric acid or ammonium nitrate. Where those components are added together, a solution obtained by dissolving nitric acid or ammonium nitrate in an aqueous solution of oxalate of Nb or Ta can be mixed with the reaction product obtained in the step (1).

The preferred amount of the Nb compound or Ta compound used is such that the atomic ratio of Nb or Ta to Mo in the resulting catalyst is from 0.001 to 3.0:1. If the ratio of Nb or Ta to Mo is below 0.01, deterioration of the resulting catalyst occurs. On the other hand, if the atomic ratio of Nb or Ta to Mo exceeds 3.0, the resulting catalyst has a low activity, leading to the reduction in conversion of propane.

The amount of nitric acid or ammonium nitrate used is preferably from 0.5 to 2.1, more preferably from 1.0 to 1.6, in terms of molar ratio to Sb to be supplied into the step (1). It is presumed that nitric acid or ammonium nitrate acts to form fine primary particles uniformly. As a result of the uniform formation of fine primary particles, a catalyst having a good abrasion resistance can be prepared with a good reproducibility. When the amount of nitric acid added is below 0.5 in terms of molar ratio to Sb, the resulting catalyst has poor reproducibility of activity and poor abrasion resistance. On the other hand, if the amount of nitric acid added exceeds 2.1, the catalyst undergoes excessive oxidation, resulting in deterioration of the activity.

In the present invention, metals other than the above metals may be used, such as Ag, Zn, Pb, Cu, Se, Tl, Na, K, Rb, Mg, Ca, Cr, W, Fe, Ru, Co and Ni. One or two or more of these metals (hereinafter occasionally referred to as "optional metals") may be used in combination with the above metals, i.e., Mo, Vi, Sb and A (A represents Nb or Ta) (hereinafter occasionally referred to as "essential metals").

The preferred amount of the optional metals used is from 0.0001 to 0.05 in terms of atomic ratio to Mo.

The time at which the compound made of the optional metals as constituents is mixed with the essential metal compound is before calcination. Specifically, it may be either at the step (1) or at the step (2). The two components are preferably mixed with each other in the presence of a liquid medium to obtain a uniform mixture.

The metal compound mixture obtained by the above operation is then optionally dried by evaporation to dryness or spray drying. The mixture thus dried is then calcined to convert it to a metal oxide having a specific crystal structure which is used as the catalyst of the present invention.

The calcining operation is preferably a combination of calcining in the presence of oxygen at a temperature of from 250° C. to 350° C., preferably from 280° C. to 320° C. for 2 to 20 hours (preferably 4 to 10 hours) and subsequent calcining in the absence of oxygen at a temperature of from 500° C. to 600° C., preferably from 570° C. to 620° C. for 1 to 3 hours.

The content of metallic elements in the metal oxide obtained by calcining can be confirmed by fluorescent X-ray analysis.

The catalyst for the production of acrylic acid prepared by the above steps (1) and (2) or steps (3) and (4) is preferably ground to an appropriate particle size, thereby increasing the surface area. The grinding method that can be used is either dry grinding method or wet grinding method. Examples of the grinding apparatus that can be used include mortar and ball mill. Examples of the solvent used as a grinding aid include water and alcohol. The amount of the solvent used is from 0.3 to 3 in terms of weight ratio to the catalyst. The particle size of the catalyst of the present invention is preferably 20 $\mu$m or less, more preferably 5 $\mu$m or less.

The catalyst thus obtained is then evaluated for abrasion resistance by the following particle size retention test.

Testing Method 2.0 g of the catalyst which has been ground to 16 to 30 mesh is put into a 300 ml vessel with a screw cap (vessel for ball mill) together with 5.0 g of steel balls having a diameter of 2.5 mm. The vessel is closed, placed on the roller of the ball mill, and then rotated at a speed of 105 rpm for 30 minutes. The content of the vessel is then sieved through a stack of a 16-mesh sieve and a 30-mesh sieve in such a manner that it is sieved through the 16-mesh sieve at first to remove the steel balls and fine powder therefrom. Thus, particles having a size of from 16 to 30 mesh are separated. The particles thus obtained are then weighed. The percentage of the weight of the particles to the original weight of the catalyst is defined as percent particle size retention.

The catalyst for the production of acrylic acid of the present invention can be used free of carrier but can also be used in the state of supporting on a carrier such as silica, alumina, silica-alumina and silicon carbide each having an appropriate particle size.

The catalyst of the present invention can be applied to the synthesis of acrylic acid involving the oxidation of propane, propylene or acrolein. The catalyst is preferably applied to oxidation of propane.

Propane and oxygen gas as raw materials of acrylic acid may be separately introduced into the reactor where they are then mixed or propane and oxygen gas may previously be mixed and the resulting mixture may be introduced into the reactor. Further, oxygen gas may be supplied to the reactor through the wall (closed on one end) of a porous ceramics tube inserted into the tubular reactor.

Examples of oxygen gas used include pure oxygen gas, air and a gas obtained by diluting these gases with nitrogen, steam or carbon dioxide gas. Where propane and air are used, the volumetric proportion of air to propane is preferably 30 times or less, more preferably from 0.2 to 20 times.

Propane as unreacted raw material and propylene as an intermediate product, obtained at the outlet of the reactor can be directly used as fuel, but can also be separated from the other components of the product and then introduced into the reactor for reuse.

The reaction temperature is preferably from 300° C. to 600° C., more preferably from 350° C. to 500° C. The optimum gas space velocity (hereinafter referred to as "SV") is from 300 to 5,000/hr.

The present invention will be described in more detail by the following examples and comparative examples, but it should be understood that the invention is not construed as being limited thereto.

The catalyst obtained in each of the examples and comparative examples was packed into a quartz tubular reactor having a diameter of 10 mm$\phi$ in an amount of 1.5 ml (about 2.22 g). A mixture of 4.4% by volume of propane, 7.0% by volume of oxygen, 26.3% by volume of nitrogen and 62.3% by volume of steam was then supplied into the reactor preheated to a temperature of 420° C., at a rate of 2,400/hr to produce acrylic acid. The conversion and selectivity were calculated based on the reaction product. These values were then used to evaluate the properties of the catalyst. The results obtained are shown in the Table below.

The conversion, selectivity and yield are calculated in the following manner (as calculated in terms of mol):

Conversion of propane (%)=(Amount of propane supplied−Amount of unreacted propane)/Amount of propane supplied Selectivity of acrylic acid (%)=Amount of acrylic acid produced/(Amount of propane supplied−Amount of unreacted propane)

Yield of acrylic acid (%)=Conversion of propane×Selectivity of acrylic acid

EXAMPLE 1

6.15 g of ammonium metavanadate was added to 130 ml of distilled water in a 300 ml glass flask and then dissolved therein under heating with stirring. 6.35 g of antimony trioxide and 30.5 g of ammonium molybdate were added to the resulting solution. A large amount of nitrogen gas was passed through the flask so that the air in the flask was thoroughly replaced by nitrogen. A mixture of air and nitrogen having an oxygen gas concentration of 15% was blown into the mixed solution comprising the above components at a flow rate of 100 ml/min while stirring the mixed solution at 360 rpm with a stirrer and also heating the mixed solution to a temperature of 92° C. The reaction was conducted for 5 hours under those conditions.

A blue colloidal dispersion thus obtained was cooled to room temperature, and an aqueous solution obtained by dissolving 13.15 g of oxalic acid, 3.25 g of niobic acid and 6.0 g of 60% concentrated nitric acid in 90 ml of distilled water was then added to the dispersion. The resulting mixed solution was vigorously stirred for 30 minutes, concentrated by heating, and then subjected to evaporation to dryness at a temperature of 120° C. The solid matter thus obtained was calcined at a temperature of 300° C. in air for 5 hours, and then calcined at a temperature of 600° C. in a stream of nitrogen gas for 2 hours to obtain a specific crystalline catalyst. The catalyst thus obtained was tabletted, ground to a particle size of from 16 to 30 mesh, and then used in the reaction for the production of acrylic acid. The atomic ratio of Mo/V/Sb/Nb of the catalyst was 1.0/0.3/0.25/0.10. As a result of the particle size retention test, the catalyst showed a particle size retention of 92.4%.

The results of the acrylic acid synthesis test using the catalyst are shown in the Table below. In the Table, AA represents acrylic acid.

EXAMPLE 2

A catalyst was prepared in the same manner as in Example 1 except that in place of 6.0 g of nitric acid, 5.0 g of ammonium nitrate was added to the solution obtained by dissolving 13.15 g of oxalic acid and 3.25 g of niobic acid in 90 ml of distilled water. The results of the acrylic acid synthesis test using the catalyst thus prepared are shown in the Table below. As a result of the particle size retention test, the catalyst showed a particle size retention of 91.5%.

EXAMPLE 3

6.15 g of ammonium metavanadate was added to 130 ml of distilled water in a 300 ml glass flask, and was dissolved therein under heating with stirring, and 5.87 g of antimony trioxide and 30.9 g of ammonium molybdate were then added to the resulting solution. A large amount of nitrogen gas was passed through the flask so that the air in the flask was thoroughly replaced by nitrogen. The mixture comprising the above components was heated under reflux in an atmosphere of nitrogen gas for 16 hours while stirring the mixture at 360 rpm by a stirrer, thereby conducting the reaction. 40 g of a 1.54 wt % hydrogen peroxide was added dropwise to the resulting reaction solution with stirring under heating over 5 hours.

The blue colloidal dispersion thus obtained was cooled to room temperature, and an aqueous solution obtained by dissolving 8.82 g of oxalic acid, 2.33 g of niobic acid and 6.0 g of 60% concentrated nitric acid in 75 ml of distilled water was then added to the dispersion. The resulting mixed solution was vigorously stirred in an atmosphere of nitrogen gas for 30 minutes, concentrated by heating, and then subjected to evaporation to dryness at a temperature of 120° C.

The solid matter thus obtained was calcined at a temperature of 300° C. in air for 5 hours, and then calcined at a temperature of 600° C. in a stream of nitrogen gas for 2 hours to obtain a metal oxide catalyst. The catalyst thus obtained was tabletted, ground to a particle size of from 16 to 30 mesh, and then used in the reaction for the production of acrylic acid. The atomic ratio of Mo/V/Sb/Nb of the catalyst was 1.0/0.3/0.23/0.08. As a result of the particle size retention test, the catalyst showed a particle size retention of 90%.

The results of the acrylic acid synthesis test using the catalyst are shown in the Table below.

Comparative Example 1

A catalyst was prepared in the same manner as in Example 1 except that nitric acid was not added to the solution obtained by dissolving 13.15 g of oxalic acid and 3.25 g of niobic acid in 90 ml of distilled water. The results of the acrylic acid synthesis test using the catalyst thus prepared are shown in the Table below. As a result of the particle size retention test, the catalyst showed a particle size retention of 70.5%.

Comparative Example 2

A catalyst was prepared in the same manner as in Example 3 except that nitric acid was not added to the solution obtained by dissolving 8.82 g of oxalic acid and 2.33 g of niobic acid in 75 ml of distilled water. The results of the acrylic acid synthesis test using the catalyst thus prepared are shown in the Table below. As a result of the particle size retention test, the catalyst showed a particle size retention of 62.5%.

TABLE 1

| Example No. | Conversion of propane (%) | Selection of AA (%) | Yield of AA (%) |
| --- | --- | --- | --- |
| Example 1 | 55.1 | 62.5 | 33.8 |
| Example 2 | 52.8 | 66.1 | 34.5 |
| Example 3 | 53.1 | 65.2 | 34.6 |
| Comparative Example 1 | 52.8 | 60.9 | 32.2 |
| Comparative Example 2 | 50.2 | 59.7 | 30.0 |

Use of the catalyst for the production of acrylic acid according to the present invention makes it possible to synthesize acrylic acid in a high yield by the vapor phase catalytic reaction of propane. Further, the catalyst of the present invention has an excellent abrasion resistance and therefore can be used over an extended period of time.

While the invention has been described in detail and with reference to specific embodiments thereof, it will be apparent to one skilled in the art that various changes and modifications can be made therein without departing from the spirit and scope thereof.

What is claimed is:

1. A process for the production of acrylic acid by a vapor phase catalytic oxidation of propane using a metal oxide catalyst comprising Mo, V, Sb and A (A represents Nb or Ta), the catalyst being obtained by a method comprising the following steps (1) and (2):

(1) a step of reacting $V^{+5}$ and $Sb^{+3}$ at a temperature of 70° C. or higher in the presence of $Mo^{+6}$ in an aqueous medium, and bubbling an oxygen-containing gas into the reaction mixture during or after the reaction; and (2) a step of adding to the reaction product obtained in step (1) a solution containing a compound comprising A and an aqueous solution of nitric acid or ammonium nitrate, uniformly stirring these components, and then calcining the resulting mixture.

2. A process for the production of acrylic acid by a vapor phase catalytic oxidation of propane using a metal oxide catalyst comprising Mo, V, Sb, and A (A represents Nb or Ta), the catalyst being obtained by a method comprising the following steps (3) and (4):

(3) a step of reacting $V^{+5}$ and $Sb^{+3}$ at a temperature of 70° C. or higher in the presence of $Mo^{+6}$ in an aqueous medium, and adding hydrogen peroxide to the reaction mixture during or after the reaction; and (4) a step of adding to the reaction product obtained in step (3) a solution containing a compound comprising A and an aqueous solution of nitric acid or ammonium nitrate, uniformly stirring these components, and then calcining the resulting mixture.

* * * * *